United States Patent [19]

Stoltefuss et al.

[11] Patent Number: 5,652,371
[45] Date of Patent: Jul. 29, 1997

[54] 3-IMINO-3-ALKOXY-PROPIONIC ACID LACTATES AND THEIR TAUTOMERIC ACRYLIC ACID LACTATES

[75] Inventors: Jürgen Stoltefuss, Haan; Michael Negele, Solingen, both of Germany

[73] Assignee: Bayer Aktiengesellschaft, Leverkusen, Germany

[21] Appl. No.: 518,126

[22] Filed: Aug. 22, 1995

Related U.S. Application Data

[63] Continuation of Ser. No. 128,956, Sep. 29, 1993, abandoned.

[30] Foreign Application Priority Data

Oct. 6, 1992 [DE] Germany .................. 42 33 586.8

[51] Int. Cl.$^6$ .................. C07C 249/02; C07C 251/08
[52] U.S. Cl. .................. 546/249; 558/6; 546/167
[58] Field of Search .................. 558/6; 546/249

[56] References Cited

U.S. PATENT DOCUMENTS

| | | | |
|---|---|---|---|
| 3,402,193 | 9/1968 | Hagemeyer et al. | 558/6 |
| 3,538,139 | 11/1970 | Hagemeyer et al. | 558/6 |
| 4,727,142 | 2/1988 | Fuss et al. | 544/216 |
| 5,225,558 | 7/1993 | Stoltefuss et al. | 546/167 |

FOREIGN PATENT DOCUMENTS 0515940  12/1992  European Pat. Off. .

OTHER PUBLICATIONS

S. A. Glickmann, A.C. Cope, J. Am. Chem. Soc. 67 (1945), 1017.

*Primary Examiner*—Johann Richter
*Assistant Examiner*—Michael G. Ambrose
*Attorney, Agent, or Firm*—Sprung Horn Kramer & Woods

[57] ABSTRACT

The invention relates to novel 3-imino-3-alkoxy-propionic acid lactates and their tautomeric acrylic acid lactates, processes for their preparation and their use as intermediates in the synthesis of 2-amino-substituted 1,4-dihydropyridines.

5 Claims, No Drawings

3-IMINO-3-ALKOXY-PROPIONIC ACID LACTATES AND THEIR TAUTOMERIC ACRYLIC ACID LACTATES

This application is a continuation, of application Ser. No. 08/128,956, filed Sep. 29, 1993, now abandoned.

The invention relates to novel 3-imino-3-alkoxy-propionic acid lactates and their tautomeric acrylic acid lactates, processes for their preparation and their use as intermediates in the synthesis of 2-amino-substituted 1,4-dihydropyridines.

Imino ethers and imino esters are already known [cf. S. A. Glickmann, A. C. Cope, J. Am. Chem. Soc. 67 (1945) 1017].

The present invention relates to novel 3-imino-3-alkoxy-propionic acid lactates and their tautomeric acrylic acid lactates of the general formula (I)

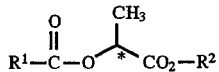
(I)

in which

R$^1$ represents a tautomeric radical of the formula

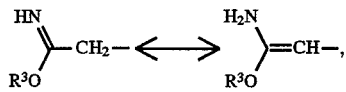

in which

R$^3$ denotes aryl having 6 to 10 carbon atoms, straight-chain or branched alkyl, alkenyl, alkadienyl or alkinyl having in each case up to 10 carbon atoms, which are optionally substituted identically or differently once or twice by halogen, hydroxyl, carboxyl, cyano, nitro, or by straight-chain or branched alkylthio, alkoxy, alkoxycarbonyl, acyl or acyloxy having in each case up to 8 carbon atoms, or by phenoxy or phenyl, it being possible for the latter, for their part, to be substituted identically or differently up to 2 times by halogen or by straight-chain or branched alkyl or alkoxy having in each case up to 6 carbon atoms, R$^2$ has the abovementioned meaning of R$^3$ and is identical to or different from the latter and salts, free bases and pure enantiomers thereof.

Salts are salts of the compounds according to the invention with inorganic or organic acids. Salts with inorganic acids, such as, for example, hydrochloric acid, hydrobromic acid, phosphoric acid or sulphuric acid, are preferred.

The compounds according to the invention exist in stereoisomeric forms which either do (enantiomers) or do not (diastereomers) relate to each other as image and mirror image. The invention relates both to the antipodes and the racemic forms, as well as to the diastereomeric mixtures. The racemic forms, just like the diastereomers, can be separated in a known manner into the stereoisomerically homogeneous components.

By way of example, this will be explained, with reference to the general formula (I), using the radicals of the formulae (II) and (IIa):

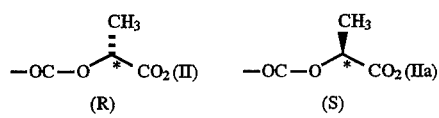

Compounds of the general formula (I) are preferred in which

R$^1$ represents a tautomeric radical of the formula

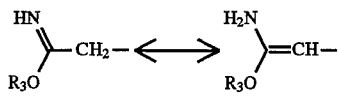

in which

R$^3$ denotes phenyl, naphthyl, straight-chain or branched alkyl or alkenyl having in each case up to 10 carbon atoms, which are optionally substituted by halogen, hydroxyl, carboxyl, cyano, or by straight-chain or branched alkylthio, alkoxycarbonyl, alkoxy, acyl or acyloxy having in each case up to 6 carbon atoms, phenoxy or phenyl, R$^2$ has the abovementioned meaning of R$^3$ and is identical to or different from the latter and salts, free bases and pure enantiomers thereof.

Compounds of the general formula (I) are particularly preferred
in which

R$^1$ represents a tautomeric radical of the formula

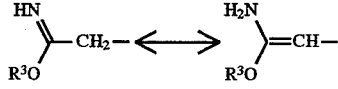

in which

R$^3$ denotes phenyl or straight-chain or branched alkyl having up to 8 carbon atoms, which are optionally substituted by fluorine, chlorine, hydroxyl, carboxyl, cyano, or by straight-chain or branched alkoxycarbonyl, alkoxy or acyloxy having in each case up to 4 carbon atoms, R$^2$ has the abovementioned meaning of R$^3$ and is identical to or different from the latter and salts, free bases and pure enantiomers thereof.

Compounds of the general formula (I) are very particularly preferred
in which

R$^1$ represents a tautomeric radical of the formula

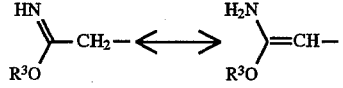

in which

R$^3$ denotes straight-chain or branched alkyl having up to 4 carbon atoms, which is optionally substituted by chlorine, fluorine, methoxy or ethoxy, R$^2$ has the abovementioned meaning of R$^3$ and is identical to or different from the latter and salts, free bases and pure enantiomers thereof.

In addition, a novel process for preparing the compounds of the general formula (I) according to the invention has been found, characterised in that compounds of the general formula (III)

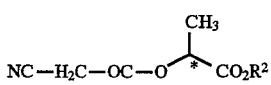

(III)

in which
R[2] has the abovementioned meaning and is preferably already present in an enantiomerically pure form (*R or S),
are first reacted with alcohols of the general formula (IV)

$$R^3{-}OH \qquad (IV)$$

in which
R[3] has the abovementioned meaning,
in inert solvents and in the presence of acids,
and, in the case of the free bases, are subsequently treated with bases.

By way of example, the process according to the invention can be illustrated by the following formula diagram:

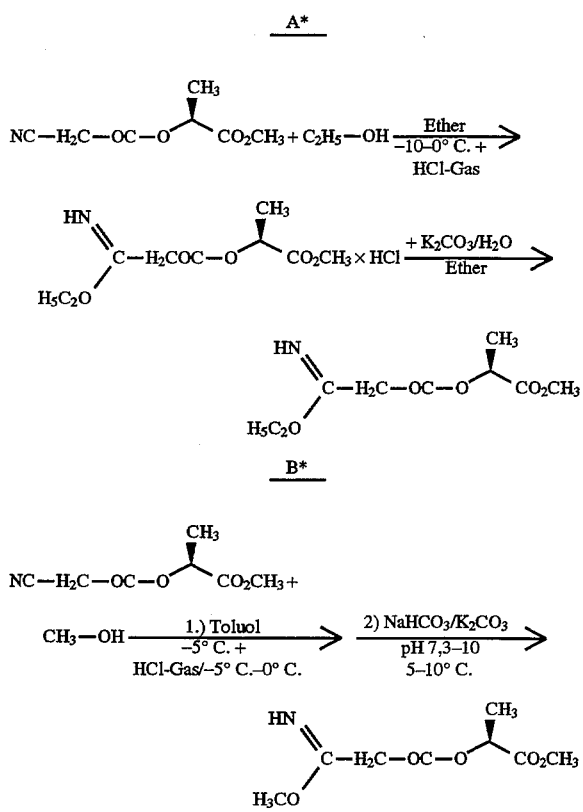

*In the following, [A] denotes the reaction of the compounds of the general formula (III) in the molar quantity range, while [B] represents the quantities for the semi-industrial scale (kg quantities).

All organic solvents which are not altered under the reaction conditions are suitable solvents. These preferably include ethers, such as diethyl ether, diisopropyl ether, methyl tert-butyl ether, dioxane, tetrahydrofuran, glycol dimethyl ether, or diethylene glycol dimethyl ether, or halogenated hydrocarbons, such as methylene chloride, carbon tetrachloride or chloroform, or hydrocarbons, such as benzene or toluene.

Diethyl ether is particularly preferred for the reaction of the compounds of the general formula (III) according to [A], as is toluene in the case of the semi-industrial reaction (kg range) according to [B].

Suitable acids are, in particular, gaseous, anhydrous hydrogen halides, such as, for example, HCl or HBr. HCl is preferred.

The reaction temperatures can be varied within a wide range. In general, a temperature range of $-25°$ C. to $+25°$ C., preferably of $-10°$ C. to $+10°$ C., is employed. A range of $-10°$ C. to $0°$ C. is particularly preferred in the case of reaction A, as is the range $-5°$ C. to $+5°$ C. in the case of reaction B.

With regard to the optimal yield of the compounds of the general formula (I) according to the invention, the reaction time lies within a range from 1 to 48 hours, preferably 4 to 24 hours.

The reaction can be carried out under atmospheric pressure, but also under elevated or reduced pressure (e.g. 0.5 to 30 bar). In general, atmospheric pressure is employed.

In general, 1 to 5 mol of the alcohols of the formula (IV) and 1–30 mol of acid, in each case based on 1 mol of the compounds of the general formula (III), are employed.

The liberation of the bases is effected, in general, using alkali metal or alkaline earth metal carbonates, such as, for example, sodium or potassium carbonate.

The novel process according to the invention is distinguished, in contrast to the state of the art, by the fact, on the one hand, that the possible known side reactions, such as, for example, cleavage of the activated esters, hydrolysis of the imino esters and/or secondary reactions of the end products, such as, for example, a base-catalysed intramolecular ester condensation, are suppressed as a consequence of the optimised conditions listed above, and, on the other hand, that the compounds of the general formula (I) according to the invention can be prepared in very good yields by a mild and elegant route.

The compounds of the general formula (I) according to the invention are valuable intermediates for the preparation of, in particular, chiral 2-amino-dihydropyridines, which are of great importance in 1,4-dihydropyridine chemistry.

The alcohols of the general formula (IV) are known.

The compounds of the general formula (III) are known in part and can be prepared by reacting cyanoacetic acid of the formula (V)

$$NC{-}CH_2{-}CO_2H \qquad (V)$$

with compounds of the general formula (VI)

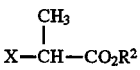

in which
R[2] has the abovementioned meaning
and
X represents chlorine or hydroxyl, preferably hydroxyl, in one of the solvents listed above, preferably tetrahydrofuran, and in the presence of a dehydrating agent.

Suitable dehydrating reagents are carbodiimides, such as, for example, diisopropylcarbodiimide, dicyclohexylcarbodiimide or N-(3-dimethylaminopropyl)-N'-ethylcarbodiimide hydrochloride, or carbonyl compounds, such as carbonyldiimidazole, or 1,2-oxazolium compounds, such as 2-ethyl-5-phenyl-1,2-oxazolium-3-sulphonate, or propanephosphonic anhydride or isobutyl chloroformate or benzotriazolyloxy-tris-(dimethylamino)phosphonium hexafluorophosphate or diphenyl phosphoramidate or methanesulphonyl chloride, optionally in the presence of bases, such as triethylamine or N-ethylmorpholine or N-methylpiperidine or dicyclohexylcarbodiimide and N-hydroxysuccinimide.

Starting compounds

EXAMPLE Z1

(S)-Methyl 2-cyanoacetoxy-propionate

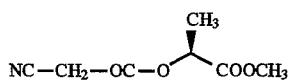

100 g (0.96 mol) of (S)-methyl lactate and 81.8 g (0.96 mol) of cyanoacetic acid are dissolved in 1 l of dry tetrahydrofuran. A solution of 198.3 g (0.96 mol) of dicyclohexylcarbodiimide in 350 ml of dry THF is added rapidly dropwise at 20° C. to 30° C. into this mixture. The mixture is subsequently stirred for 30 minutes and filtered with suction to remove the precipitated dicyclohexylurea, which is washed with THF. The filtrate is concentrated and the oil which is obtained is distilled. 302 g (91.8% of theory) of a colourless oil are obtained with a boiling point of 110°–112° C. at 0.2 mbar.

PREPARATION EXAMPLES

Example 1

(S)-1-(Methoxycarbonyl)ethyl 3-imino-3-ethoxy-propionate hydrochloride

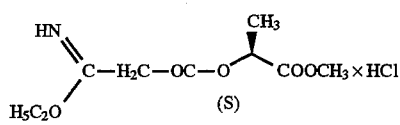

322 g (1.8 mol) of the compound from Example Z1 are dissolved in 1.2 l of dry ether and 132 ml (2.26 mol) of ethanol. Dry hydrogen chloride gas is passed in at −10° C. to 0° C. until saturation is achieved. The mixture is stirred at 0° C. overnight and concentrated in vacuo. About 476 g of a semi-solid oil are obtained.

Example 2

(S)-1-(Methoxycarbonyl)-ethyl 3-imino-3-ethoxy-propionate

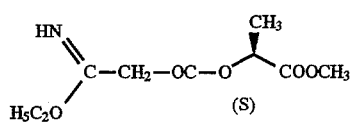

476 g of the compound from Example 1 are stirred, at 10°–15° C., into a solution of 300 g of potassium carbonate in 1 l of water, and 1.5 l of diethyl ether are added. While stirring, the aqueous phase is made slightly alkaline by the addition of a saturated potassium carbonate solution. During this process, the major part of the base which is sought crystallises out. It is filtered off with suction and washed with ether. The ether phase of the filtrate is separated from the aqueous phase, dried, concentrated, stirred with a little cold ether, and filtered with suction. 380 g (93% of theory) of colourless crystals are obtained with a melting point of 90°–92° C.

The compounds listed in Table 1 are prepared in analogy with the instructions of Examples 1 and 2:

TABLE 1

$$\text{HN}=\text{C}(\text{OR}_3)-\text{CH}_2-\text{CO}_2-\text{Y}-\text{CO}_2-\text{R}_2$$

| Ex. No. | R³ | Y(Enantiomer) | R² | Salt/Base | m.p. °C. | Yield % of theory |
|---|---|---|---|---|---|---|
| 3 | —C₂H₅ | CH₃ ↓ C (S) | —C₂H₅ | base | Öl | 85,2% |
| 4 | —C₂H₅ | CH₃ ⋮ C (R) | CH₂—CH(CH₃)₂ | HCl | 92 | 94% |
| 5 | —C₂H₅ | CH₃ ↓ C (S) | —CH(CH₃)₂ | base | Öl | 82% |

Example 6

(S)-1-(Methoxycarbonyl)ethyl 3-imino-3-methoxypropionate

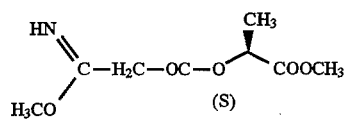

8.55 kg (50 mol) of (S)-methyl 2-cyanoacetoxy-propionate and 2.12 kg (66.13 mol) of methanol in 12 ltr. of toluene are introduced at −5° C. (jacket cooling) into a 25 ltr. stirred vessel (enamel). Within 4 h, and while stirring, about 4.5 kg of hydrogen chloride (120 mol) are passed in at such a speed that the temperature does not rise above 0° C. and the HCl is absorbed to the greatest extent possible. After saturation, the mixture is subsequently stirred at about 5° C. overnight while retaining the external cooling. To liberate the imino ester, the reaction solution is stirred, at 5°–10° C., into a solution of NaHCO$_3$/K$_2$CO$_3$ (5 kg of NaHCO$_3$; 2.8 kg of K$_2$CO$_3$ in 30 l of water) adjusted to pH 10. The pH rapidly comes to 7.5, and must, where appropriate, be corrected by addition of further K$_2$CO$_3$ solution. The free imino ester crystallises out and, after a further stirring period of about 1 h, is filtered off with suction. The crystals are subsequently washed twice with 10 ltr. of water each time and dried at 40° C. in vacuo overnight.

Yield: 7.52 kg (74% of theory) of crystals M.p.: 81°–82° C.

A further 165 g (1.6% of theory) are obtained from the toluene phase following concentration.

We claim:

1. A symmetrical alkyl 3-imino-3-alkoxy-propionic acid lactate or its tautomeric symmetrical acrylic acid lactate of the formula (I):

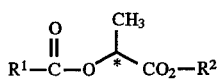

in which

R$^1$ represents a tautomeric radical of the formula:

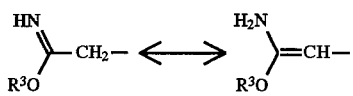

and

R$^2$ and R$^3$ are identical and both are methyl or both are ethyl;

or a salt, free base or enantiomer thereof.

2. The compound according to claim 1, which has the formula:

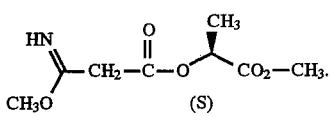

3. The compound according to claim 1, which has the formula:

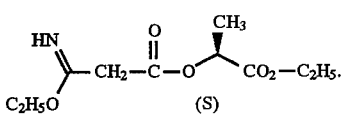

4. A process for preparing a symmetrical alkyl 3-imino-3-alkoxy-propionic acid lactate or its tautomeric symmetrical acrylic acid lactate of the formula (I):

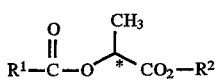

in which

R$^1$ represents a tautomeric radical of the formula:

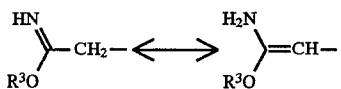

and

R$^2$ and R$^3$ are identical and both are methyl or both are ethyl;

or a salt, free base or enantiomer thereof, said process comprising the following steps:

(A) reacting a compound of the formula (III):

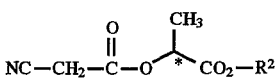

in which

R$^2$ has the abovementioned meaning, optionally in an enantiomerically pure form (*R or S), with a compound of the formula (IV):

in which

R$^3$ has the abovementioned meaning, in an inert solvent and in the presence of an acid, and, (B) in the case of a free base, subsequent treatment with a base.

5. In the process of preparing a 2-amino-substituted-1,4-dihydropyridine comprising the reaction of an alkyl 3-imino-3-alkoxy-propionic acid lactate or its tautomeric acrylic acid lactate, wherein the improvement comprises using as said 3-imino-3-alkoxy-propionic acid lactate or said tautomeric acrylic acid lactate a symmetrical alkyl 3-imino-3-alkoxy-propionic acid lactate or its tautomeric symmetrical acrylic acid lactate of the formula (I):

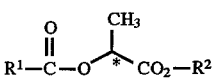

in which

R$^1$ represents a tautomeric radical of the formula:

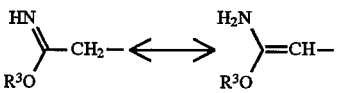

and

R$^2$ and R$^3$ are identical and both are methyl or both are ethyl;

or a salt, free base or enantiomer thereof.

* * * * *